(12) United States Patent
Sakai et al.

(10) Patent No.: US 7,130,044 B2
(45) Date of Patent: Oct. 31, 2006

(54) ATOMIC ABSORPTION SPECTROPHOTOMETER

(75) Inventors: Masumi Sakai, Kyoto (JP); Tsutomu Watanabe, Ikoma (JP); Koki Yamamoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 422 days.

(21) Appl. No.: 10/827,685

(22) Filed: Apr. 19, 2004

(65) Prior Publication Data

US 2004/0223153 A1    Nov. 11, 2004

(30) Foreign Application Priority Data

Apr. 25, 2003  (JP) ............... 2003-122259

(51) Int. Cl.
*G01J 3/42* (2006.01)
(52) U.S. Cl. ............ 356/319; 356/312; 356/311; 356/326
(58) Field of Classification Search ............ 356/305, 356/308, 311, 312, 319, 326, 328
See application file for complete search history.

(56) References Cited

U.S. PATENT DOCUMENTS 5,018,856 A * 5/1991 Harnly et al. ............ 356/312
5,579,104 A * 11/1996 Honda et al. ............ 356/73
5,861,949 A * 1/1999 Kojima ............ 356/328
6,683,685 B1 * 1/2004 Sakai ............ 356/307

FOREIGN PATENT DOCUMENTS

| JP | 06-094606 | 4/1994 |
|---|---|---|
| JP | 2002-071558 | 3/2002 |

* cited by examiner

*Primary Examiner*—Layla G. Lauchman
(74) *Attorney, Agent, or Firm*—Rankin, Hill, Porter & Clark, LLP

(57) ABSTRACT

At the time of measurement of a sample, before a sample is introduced into a graphite tube, signal voltages which would be detected by a photomultiplier in connection with all programmable combinations of atomizing temperatures of a graphite tube, widths of entrance and exit slits provided in a spectrometer, and wavelengths into which the light is to be decomposed by the diffraction grating are stored in memory beforehand. At the time of measurement of a sample, an amplification factor of the photomultiplier is controlled by a negative high-voltage controller according to measurement requirements, or measurement is performed after an optimum detector signal voltage is set by controlling the amplification factor of the detector signal output from an amplifier.

1 Claim, 2 Drawing Sheets

FIG. 2

| WAVELENGTH | ATOMIZING TEMPERATURE | SLIT WIDTH | DETECTOR SIGNAL VOLTAGE |
|---|---|---|---|
| 190-400nm | 2600°C OR LESS | 0.2mm | 6.0V |
| | | 0.7mm | 6.0V |
| | 2600-2700°C | 0.2mm | 6.0V |
| | | 0.7mm | 5.0V |
| | 2700°C OR MORE | 0.2mm | 4.0V |
| | | 0.7mm | 3.0V |
| 400-900nm | 2600°C OR LESS | 0.2mm | 6.0V |
| | | 0.7mm | 5.5V |
| | 2600-2700°C | 0.2mm | 5.0V |
| | | 0.7mm | 4.0V |
| | 2700°C OR MORE | 0.2mm | 3.0V |
| | | 0.7mm | 2.0V |

ATOMIC ABSORPTION SPECTROPHOTOMETER

BACKGROUND OF THE INVENTION

1. Field of the Invention

The present invention relates to an atomic absorption spectrophotometer which performs quantitative analysis of metal elements contained in various substances, and more particularly, to a furnace-type atomic absorption spectrophotometer.

2. Description of the Related Art

In an atomic absorption spectrophotometer, light originating from a holocathode lamp which serves as a light source is decomposed into spectra by a spectrometer, and the spectra reach a detector. A detector signal voltage is dependent on the type of an element of the holocathode lamp, a characteristic of the spectrometer, and a spectral sensitivity characteristic of the detector.

In the furnace-type atomic absorption spectrophotometer, a sample is held in a graphite tube (heating tube), and the tube is heated, whereby the sample is heated to a high temperature and eventually atomized. A measuring beam is caused to pass through atomic vapors, to thus measure absorbancy. Therefore, when the graphite tube has reached the maximum temperature; that is, when the sample is atomized, the graphite tube radiates light. The thus-emitted light also reaches the detector.

The detection signal including the emitted light may saturate an analog circuit or may exceed the maximum voltage which can be converted by an analog-to-digital converter, because the detection signal is excessively strong. However, when the detection signal has exceeded the maximum voltage, accurate measurement of the signal cannot be carried out. For this reason, an optimum detection signal voltage is set by controlling an amplification factor of the detection signal before measurement (see, e.g., JP-A-2002-71558).

This detection signal voltage is usually set to 50 to 70% of the maximum voltage which can be measured within the atomic absorption spectrophotometer. In consideration of noise of the analog circuit or quantization noise of the analog-to-digital converter, both being employed in the atomic absorption spectrophotometer, a better signal-to-noise ratio is obtained as the voltage of the detection signal approaches 100%. However, in order to prevent saturation of the voltage of the detection signal, which would otherwise be caused by the light emitted from the graphite tube, the voltage is held down to 50 to 70% of the maximum voltage.

Under the related-art method, only a given margin for the light emitted from the graphite tube is expected within an ordinary range of measurement requirements, and no allowance is given for variations in the intensity of emitted light which would arise depending on measurement requirements. The longer the wavelength, the wider the slit width, and the higher the atomizing temperature, the greater the intensity of the light emitted from the graphite tube. Therefore, the voltage of the detection signal may exceed the maximum measurable voltage, depending on the wavelength, the slit width, and the atomizing temperature.

In such a state, the voltage has been adjusted by the operator manually rendering the slit width narrow. However, when the slit width has been made narrow, the quantity of light entering the detector is decreased, whereby the signal-to-noise ratio is deteriorated.

According to another method, an amplification factor is changed during the course of atomizing operation in response to the detector signal. However, atomization arises during a period of one second or thereabouts, thus raising demand for a circuit which is highly responsive such that it can set the amplification factor in response to the atomization. Further, the amplification factor to be set also requires accuracy, and hence such a circuit becomes expensive.

SUMMARY OF THE INVENTION

An object of the present invention is to provide a furnace-type atomic absorption spectrophotometer capable of inexpensively improving a signal-to-noise ratio without saturating a detector signal.

To solve the problem, the invention provides an atomic absorption spectrophotometer comprising:

a light source;

an atomizing section for atomizing a sample;

a spectrometer having a slit and a diffraction grating for extracting a specific wavelength from light originating from said light source;

a detector for measuring the intensity of said light having passed through said sample to output an electric signal;

an amplifier for amplifying the electric signal;

a storing unit for storing detector signal voltages corresponding to all programmable combinations of measurement wavelengths, slit widths of said slit, and atomizing temperatures of said atomizing section; and an amplification factor control unit for controlling said amplifier with an optimum detector signal amplification factor on the basis of the detector signal voltage corresponding to a measurement wavelength, a slit width, and an atomizing temperature, all being employed for measuring a sample during a sample measurement operation.

In relation to the measurement wavelength, the slit width, and the atomizing temperature of the atomizing section, all affecting the magnitude of the signal voltage of the detector, detector signal voltages corresponding to all programmable combinations of wavelengths, slit widths, and atomizing temperatures are measured before measurement of a sample, and data pertaining to the combinations are stored in memory provided in the atomic absorption spectrophotometer. When a sample is measured, the wavelength, the slit width, and the atomizing temperature have already been evident before measurement. Hence, an amplification factor of the detector signal is controlled on the basis of the signal voltage corresponding to the three measurement requirements stored in the memory, thereby setting the previously-described optimum detector signal voltage and starting measurement. As a result, the signal-to-noise ratio can be improved without saturation of the detector signal. Every time any of the three measurement requirements; that is, the wavelength, the slit width, and the atomizing temperature, is changed, the amplification factor is controlled to an optimum value, thereby enabling measurement of a sample at the highest signal-to-noise ratio.

An electrical signal obtained through photo-electric conversion performed by the photo detector is amplified by the amplifier, whereby the signal is converted into a digital signal by the analog-to-digital converter. A computer including a CPU can be used as a unit for storing the detector signal voltages corresponding to all programmable combinations of wavelengths, slit widths, and atomizing temperatures of the atomizing section.

In many cases, the atomic absorption spectrophotometer uses a photomultiplier tube (PMT) for the detector. The amplification factor of the detector is dependent on a negative high voltage applied to the PMT. Since the amplification factor can be controlled readily by adjustment of the negative high voltage, a negative high voltage controller can be used as amplification factor control unit. In addition, a voltage amplifier may be disposed in the analog circuit, and the amplification factor of the voltage amplifier may be controlled.

BRIEF DESCRIPTION OF THE DRAWINGS

FIG. 2 shows an example of optimum detection signal voltages in correspondence to respective wavelengths, slit widths, and atomizing temperatures.

DETAILED DESCRIPTION OF THE INVENTION

Figure 1:
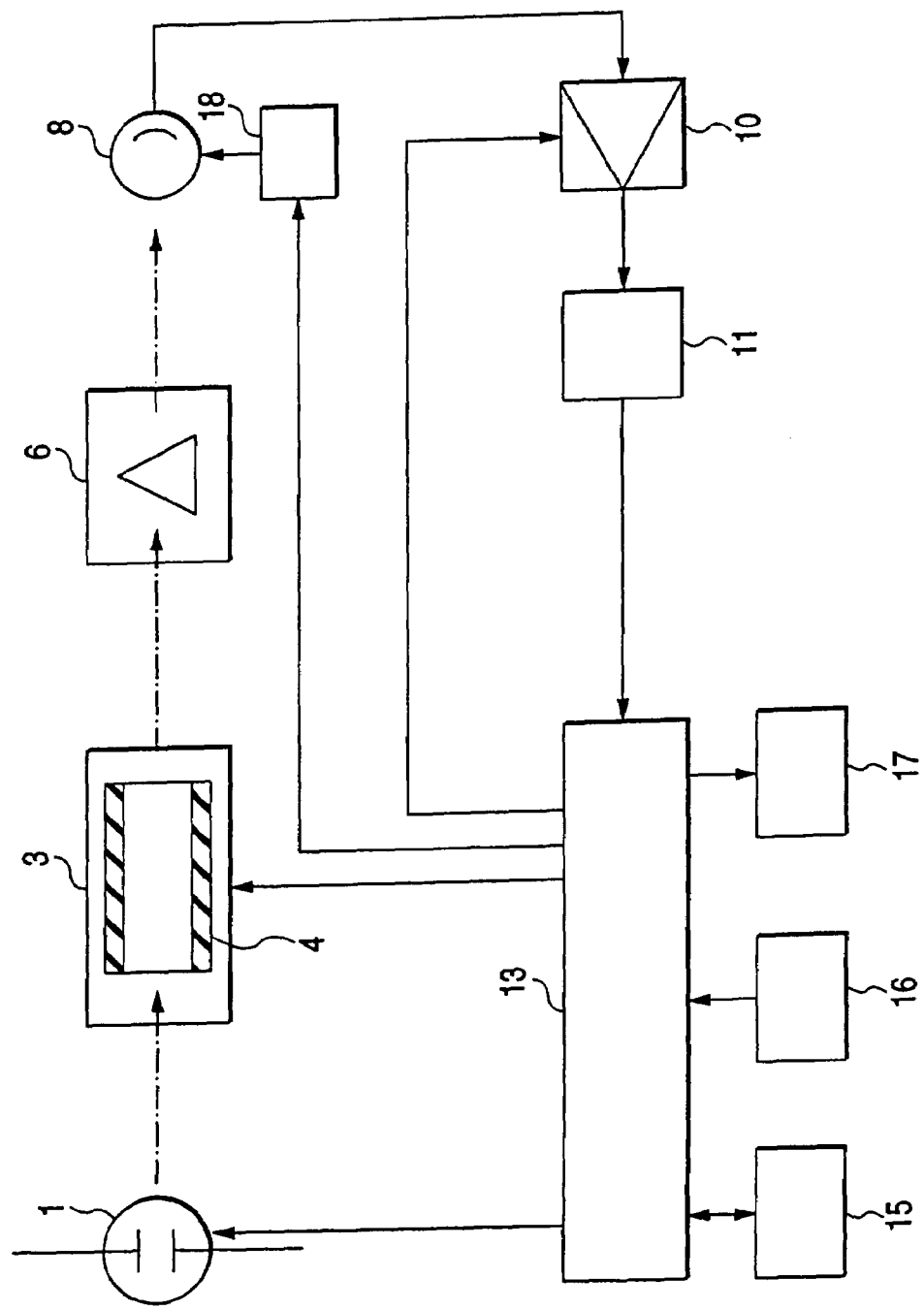
FIG. 1 is a schematic block diagram showing an embodiment of an atomic absorption spectrophotometer of the invention.

An embodiment of the present invention will be described in detail. FIG. 1 is a schematic block diagram showing an embodiment of an atomic absorption spectrophotometer of the invention. The atomic absorption spectrophotometer of the invention comprises a holocathode 1 serving as a light source; an atomizing section 3; a spectrometer 6; a photomultiplier tube 8; an amplifier 10; an analog-to-digital converter 11; a processing/control section 13; memory 15; an operation section 16; a display section 17; and a negative high-voltage controller 18. A graphite tube 4 is disposed in the atomizing section 3. The spectrometer 6 is a Zerni Turner spectrometer and comprises an entrance slit, a reflection mirror, a diffraction grating, and an exit slit.

The light, which is emitted from the holocathode lamp 1 and includes line spectra, is introduced into the spectrometer 6 after having passed through the graphite tube 4 of the atomizing section 3. The thus-introduced light passes through the entrance slit and is reflected by the reflection mirror. Subsequently, the thus-reflected light is decomposed into spectra of predetermined wavelengths by the diffraction grating, and the spectra reach the photomultiplier 8 by way of the exit slit. Although not illustrated, appropriate light-condensing optical systems are interposed between the holocathode lamp 1 and the atomizing section 3 and between the atomizing section 3 and the spectrometer 6, respectively, whereby a luminous flux is converged appropriately, and the thus-converted light is guided to the next stage. An electrical signal obtained as a result of the light having undergone photo-electric conversion performed in the photomultiplier 8 is amplified by the amplifier 10, and the thus-amplified signal is converted into a digital signal by the analog-to-digital converter 11, whereupon the signal is input to the processing/control section 13. The processing/control section 13 is constituted primarily of a computer, including a CPU, and performs various arithmetic operations and outputs a control signal for controlling operations of the individual sections. The processing/control section is connected to the memory 15, the operation section 16 including a keyboard or the like, and the display section 17 including a CRT display or the like.

A sample solution is poured into a sample inlet port (not shown) formed in an upper portion of the graphite tube 4 at the time of quantitative analysis of a sample. A heavy current is caused to flow into the graphite tube 4 from an unillustrated current source, to thus heat and atomize the sample. As mentioned previously, in the light passing through the graphite tube 4, a light having wavelength unique to the elements contained in the sample is highly absorbed. The processing/control section 13 computes a ratio of the intensity of received light achieved when the light has not been subjected to absorption to the intensity of received light achieved when the light has been subjected to absorption and performs quantitative analysis of the sample from the thus-computed absorbency.

At the time of measurement of a sample, before a sample is introduced into the graphite tube 4, signal voltages, which would be detected by the photomultiplier 8 in connection with all programmable combinations of atomizing temperatures of the graphite tube, the widths of the entrance and exit slits provided in the spectrometer 6, and wavelengths into which the light is to be decomposed by the diffraction grating, are stored in the memory 15. FIG. 2 shows an example of optimum detection signal voltages corresponding to respective wavelengths, slit widths, and atomizing temperatures. The detection signal voltages shown in FIG. 2 are sorted according to a wavelength, a slit width, and an atomizing temperature. In consideration of a margin for various variations, values are 50 to 70% of actually measured results. The settings are stored in the memory 15. At the time of measurement of a sample, the amplification factor of the photomultiplier 8 is controlled by the negative high-voltage controller 18 according to measurement requirements, or measurement is performed after an optimum detector signal voltage shown in FIG. 2 is set by controlling the amplification factor of the detector signal output from the amplifier 10. As a result, even when the voltage of the detector signal has been increased under influence of the light emitted from the graphite tube 4, the voltage of the detector signal is not saturated, and measurement can be performed at a superior signal-to-noise ratio.

Although the embodiment of the invention has been described thus far, the invention is susceptible to various modifications within the gist of the invention defined in claims. For example, sorting of the voltage of the detection signal is not limited to the wavelengths, the slit widths, and the atomizing temperatures shown in FIG. 2, but the voltage may be sorted into more detailed categories. As a result, control of the amplification factor of the amplifier 10 performed at the time of actual measurement of a sample can be performed more elaborately, and the signal-to-noise ratio can be improved to a great extent.

In many cases, an apparatus of this type, which is available in the related-art, can implement the functions of the present invention by changing only software having control programs described therein. Therefore, great increases in the cost and size of existing apparatus are not required.

According to the invention, in relation to the measurement wavelength, the slit width, and the atomizing temperature of the atomizing section, all affecting the magnitude of the signal voltage of the detector, detector signal voltages corresponding to all programmable combinations of wavelengths, slit widths, and atomizing temperatures are measured before measurement of a sample, and data pertaining to the combinations are stored in memory provided in the atomic absorption spectrophotometer. When a sample is measured, an amplification factor of the detector signal is controlled on the basis of the signal voltages stored in the memory in correspondence to the requirements; that is, the wavelength, the slit width, and the atomizing temperature, thereby setting an optimum detector signal voltage. As a result, the signal-to-noise ratio can be improved without saturation of the detector signal.

What is claimed is:

1. An atomic absorption spectrophotometer comprising:

a light source;

an atomizing section for atomizing a sample;

a spectrometer having a slit and a diffraction grating for extracting a specific wavelength from light originating from said light source;

a detector for measuring the intensity of said light having passed through said sample to output an electric signal;

an amplifier for amplifying the electric signal;

a storing unit for storing detector signal voltages corresponding to all programmable combinations of measurement wavelengths, slit widths of said slit, and atomizing temperatures of said atomizing section; and an amplification factor control unit for controlling said amplifier with an optimum detector signal amplification factor on the basis of the detector signal voltage corresponding to a measurement wavelength, a slit width, and an atomizing temperature, all being employed for measuring a sample during a sample measurement operation.

* * * * *